United States Patent
Tokita et al.

(10) Patent No.: US 9,939,367 B2
(45) Date of Patent: Apr. 10, 2018

(54) OBJECT INFORMATION ACQUIRING APPARATUS

(71) Applicant: CANON KABUSHIKI KAISHA, Tokyo (JP)

(72) Inventors: Toshinobu Tokita, Kyoto (JP); Masato Yajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 158 days.

(21) Appl. No.: 14/482,022

(22) Filed: Sep. 10, 2014

(65) Prior Publication Data
US 2015/0090037 A1    Apr. 2, 2015

(30) Foreign Application Priority Data
Sep. 30, 2013 (JP) .................................. 2013-204513

(51) Int. Cl.
*G01N 21/17* (2006.01)
*A61B 5/00* (2006.01)
*G01N 33/72* (2006.01)

(52) U.S. Cl.
CPC ....... *G01N 21/1702* (2013.01); *A61B 5/0095* (2013.01); *G01N 33/721* (2013.01);
(Continued)

(58) Field of Classification Search
CPC ......... G01N 2021/1704; G01N 33/721; G01N 2021/1706; G01N 21/274; G01N 21/278;
(Continued)

(56) References Cited

U.S. PATENT DOCUMENTS

2008/0071172 A1    3/2008  Bruck et al. ................. 600/438
2011/0172513 A1*   7/2011  Nakajima ............ A61B 5/0059
                                                    600/407
(Continued)

FOREIGN PATENT DOCUMENTS

CN    102949177    3/2013
CN    103134755    6/2013
(Continued)

OTHER PUBLICATIONS

Office Action dated Mar. 30, 2016 in P.R. China patent application 201410500266.2, with translation.
(Continued)

*Primary Examiner* — Manish S Shah
*Assistant Examiner* — Suman K Nath
(74) *Attorney, Agent, or Firm* — Fitzpatrick, Cella, Harper & Scinto

(57) ABSTRACT

An object information acquiring apparatus is used, including: an optical transmission system for transmitting light from a light source; a photoacoustic probe including an irradiating end for irradiating an object with light and a receiver for receiving acoustic waves generated from the object that has been irradiated with light; a processor for acquiring information on the object based on the acoustic waves; a light quantity meter for measuring the quantity of light emitted from the irradiating end; a memory for storing a measurement value; and a presentation unit. The processor compares the measurement value with a reference value of light quantity or a history of measurement value stored in the memory, and provides a result regarding whether or not the measurement value is within a reference range to the presentation unit.

20 Claims, 14 Drawing Sheets

STATE 1
(PHOTOACOUSTIC MEASUREMENT STANDBY MODE)

STATE 2
(PHOTOACOUSTIC MEASURING MODE)

(52) U.S. Cl.
CPC .............. *A61B 2560/0223* (2013.01); *G01N 2021/1706* (2013.01); *G01N 2201/067* (2013.01)

(58) Field of Classification Search
CPC .......... G01N 29/2418; G01N 2201/067; A61B 2560/0223
USPC .......................... 73/643; 600/407; 250/252.1
See application file for complete search history.

(56) References Cited

U.S. PATENT DOCUMENTS

| | | | |
|---|---|---|---|
| 2011/0230762 A1 | 9/2011 | Tokita et al. | 600/437 |
| 2011/0245667 A1 | 10/2011 | Tokita | 600/437 |
| 2011/0270071 A1* | 11/2011 | Furukawa | A61B 5/0095 600/407 |
| 2012/0150012 A1 | 6/2012 | Fujimoto et al. | 600/407 |
| 2012/0238859 A1 | 9/2012 | Tokita et al. | 600/407 |
| 2013/0006090 A1 | 1/2013 | Miyasato | 600/407 |
| 2013/0042688 A1 | 2/2013 | Luo et al. | 73/606 |
| 2013/0074602 A1* | 3/2013 | Jackson | G01N 29/28 73/633 |
| 2013/0116538 A1* | 5/2013 | Herzog | A61B 8/4254 600/407 |
| 2013/0144149 A1 | 6/2013 | Luo et al. | 600/407 |
| 2013/0167648 A1 | 7/2013 | Tokita | 73/655 |
| 2013/0237800 A1 | 9/2013 | Yamamoto | 600/407 |
| 2014/0046166 A1 | 2/2014 | Tokita | 600/407 |
| 2014/0051971 A1 | 2/2014 | Tokita | 600/407 |
| 2014/0114170 A1 | 4/2014 | Tokita et al. | 600/407 |
| 2014/0114171 A1 | 4/2014 | Tokita | 600/407 |

FOREIGN PATENT DOCUMENTS

| | | | | |
|---|---|---|---|---|
| JP | 2011-229756 | 11/2011 | | |
| JP | 2012-103107 | 5/2012 | | |
| JP | 2012103107 A | * 5/2012 | ............ | G01M 11/00 |
| JP | 2013-183915 | 9/2013 | | |
| WO | WO 2012/117719 A | 9/2012 | | |
| WO | WO 2013/188714 | 12/2013 | | |
| WO | WO 2014/144359 | 9/2014 | | |

OTHER PUBLICATIONS

S. Ermilov et al., "Development of Laser Optoacoustic and Ultrasonic Imaging System for Breast Cancer Utilizing Handheld Array Probes", *Photons Plus Ultrasound: Imaging and Sensing 2009, Proc. of SPIE*, vol. 7177, 2009, pp. 717703-1-717703-10 (2009).
EESR dated Dec. 4, 2014 in counterpart EPA 14194179.1.
European Office Action dated Apr. 21, 2016 in European patent application 14184179.1 (in English).
JPO Office Action dated Jul. 4, 2017, in counterpart Japanese patent application 2013-204513, with machine translation.

\* cited by examiner

OBJECT INFORMATION ACQUIRING APPARATUS

BACKGROUND OF THE INVENTION

Field of the Invention

The present invention relates to an object information acquiring apparatus.

Description of the Related Art

Photoacoustic tomography (hereinafter, called "PAT") is attracting attentions as a technique for specifically imaging angiogenesis associated with cancer. In PAT, light (near infrared light) is irradiated on an object, which in turn generates from a depth therein photoacoustic waves to be received by an ultrasonic probe for imaging.

A schematic view of a handheld photoacoustic apparatus described in non-patent literature 1 is shown in FIG. 7. A photoacoustic probe 104 has a configuration in which a receiver 106 for receiving photoacoustic waves is sandwiched and fixed by irradiating ends 103b of fiber bundles 103 of an illuminating optical system. At an incident end 103a of the fiber bundle 103, light from a light source 101 enters. The light passes through the fiber bundles 103 and irradiates an object from the irradiating ends 103b. This induces generation of photoacoustic waves from the interior of the object due to the photoacoustic effect, which photoacoustic waves are received by the receiver 106.

The received signal is converted into an electrical signal, which then undergoes amplification, digitization, and image reconstruction by a processor 107 of an ultrasonic apparatus (US). The configured image information (IMG) is transmitted to a monitor 108, which serves as a display unit, and displayed as a photoacoustic image.

Non Patent Literature 1: S. A. Ermilov et al., "Development of laser optoacoustic and ultrasonic imaging system for breast cancer utilizing handheld array probes", Photons Plus Ultrasound: Imaging and Sensing 2009, Proc. of SPIE vol. 7177, 2009.

SUMMARY OF THE INVENTION

However, the following problems have been associated with the prior art.

Over repeated photoacoustic measurements, the total quantity of light emitted from an irradiating end of a photoacoustic probe 104 may decrease due to the wear of a light source or a failure of an optical transmission system, but the decrease or the failure may be left unnoticed.

If the decreased quantity of light is ascribable to the wear of a light source 101, it can be spotted by providing a photometer (not shown) between the light source 101 and the incident end 103a.

However, the above-mentioned configuration does not make it possible to notice the occurrence of decrease in a total light quantity due to a malfunction of an optical transmission system as represented by disconnection in the fiber bundle 103, and displacement of an optical element (not shown). Consequently, photoacoustic signals are regarded to exhibit a sufficient quantity of light even though their actual quantity of light is lower. As a result, images and data, such as an absorption coefficient of an absorber as a signal source of photoacoustic waves obtained by correcting photoacoustic signals using light quantities, will become smaller than they actually are. Thus, the reliability of data and images will suffer.

The above-mentioned problems are not only for photoacoustic techniques but also have been common among other optical imaging techniques using a relatively high energy density, such as diffuse optical imaging (DOI).

The present invention addresses the above problems with an objective of enabling acquisition of reliable photoacoustic data by means of keeping track of the quantity of light emitted from an irradiating end of a probe.

The present invention provides an object information acquiring apparatus comprising:

an optical transmission system for transmitting light from a light source;

a photoacoustic probe including an irradiating end for irradiating an object with the light and a receiver for receiving acoustic waves generated by the object that has been irradiated with the light;

a processor for acquiring information on the object based on the acoustic waves;

a light quantity meter for measuring a quantity of light emitted from the irradiating end;

a memory for storing a measurement value measured by the light quantity meter; and a presentation unit, wherein the processor compares the measurement value with a reference value of light quantity or a history of measurement value stored in the memory to determine whether or not the measurement value is within a reference range, and has the presentation unit present a result of the determination thereon.

In accordance with the invention, the quantity of light emitted from an irradiating end of a probe is kept track of so that reliable photoacoustic data is provided.

Further features of the present invention will become apparent from the following description of exemplary embodiments with reference to the attached drawings.

DESCRIPTION OF THE EMBODIMENTS

Preferred embodiment of the invention will now be described with reference to the drawings. It is noted that, the dimensions, materials, shapes, and relative positions of the components described herein should be suitably modified depending on the configuration and conditions of an apparatus to which the invention is applied, and are not intended to limit the scope of the invention to the description herein.

The term "acoustic waves" as used herein includes sound waves, ultrasonic waves, photoacoustic waves, elastic waves called photo-ultrasound waves, and compressional waves. An object information acquiring apparatus of the invention is a photoacoustic tomography apparatus for acquiring information about properties inside an object by irradiating (electromagnetic) light to the object to thereby induce generation of acoustic waves in the object due to the photoacoustic effect, and receiving the generated acoustic waves.

The information about the properties of an object obtained with PAT is object information that reflects an initial acoustic pressure of acoustic waves generated due to irradiation, an absorption density and absorption coefficient of light energy derived from the initial sound pressure, levels of substances constituting the object's tissue, and the like.

Examples of substance levels include an oxygen saturation level, oxyhemoglobin level, or deoxyhemoglobin level. The property information obtained can be stored and used as numerical data, information about distribution of different locations within the object, and image data for displaying image.

The invention will be described in detail with reference to the drawings. In some cases, the same components may be provided with the same reference numbers so that detailed explanation is omitted. The invention also directs to an object information acquiring apparatus and methods for operating and controlling the same. Further, the invention also directs to programming for an information processor or the like to execute control.

Figure 1A:
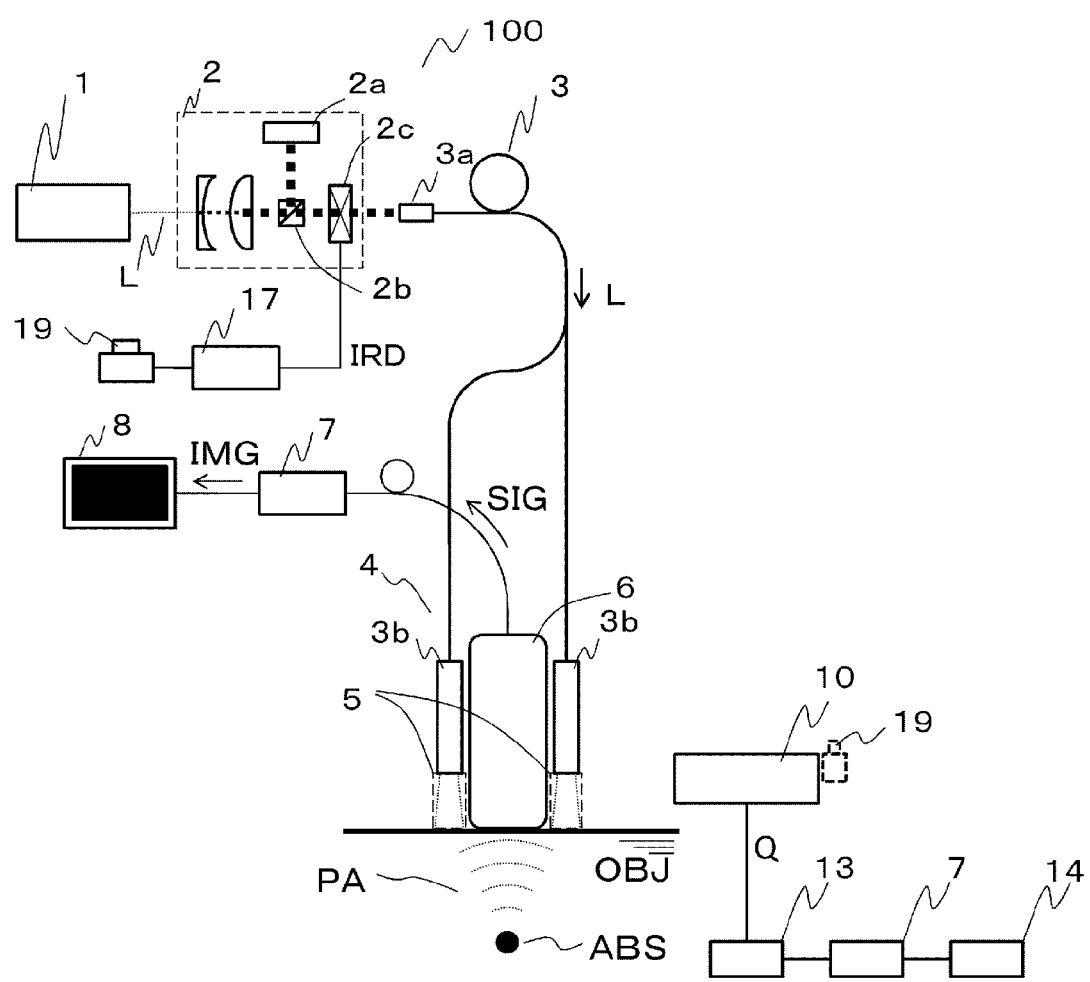
FIG. 1A is a view illustrating a configuration of a photoacoustic apparatus according to an embodiment of the invention.
Figure 1B:
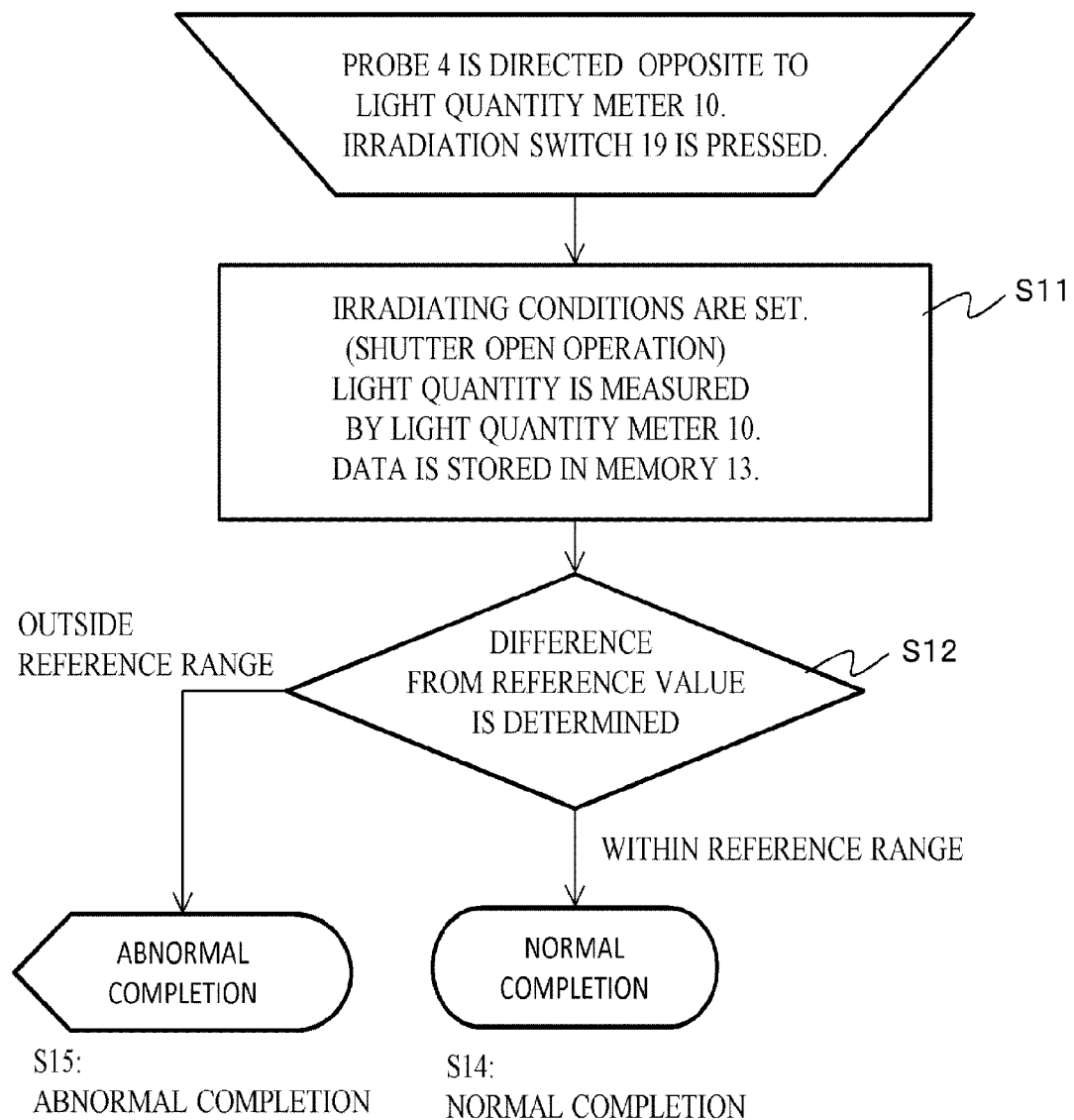
FIG. 1B is a flow chart illustrating operation of the photoacoustic apparatus according to the embodiment of the invention.

Referring to FIGS. 1A and 1B, an embodiment of the invention will now be described.

FIG. 1A is a schematic view of a photoacoustic apparatus 100. A light source 1 emits light (L). A first illuminating optical system 2 forms light that enters at an incident end 3a of a fiber bundle 3. The fiber bundle 3 transmits the light to a photoacoustic probe 4, and irradiates the light from irradiating ends 3b.

The photoacoustic probe 4 includes the irradiating ends 3b of the fiber bundle 3, second illuminating optical systems 5 for shaping the light emitted from the irradiating ends 3b, and a receiver 6 for receiving photoacoustic waves. Upon irradiation onto an object (OBJ) via the second illuminating optical systems 5, light scatters within the object and absorbed in an absorber (ABS), which in turn generates photoacoustic waves (PA).

The photoacoustic waves are converted into an electric signal (SIG) by an element contained in the receiver 6, such as a piezoelectric element, CMUT, or the like, which electrical signal is then transmitted to a processor 7. The processor 7 amplifies the electrical signal, creates image information (IMG) through digital conversion and filtering, and has the image displayed on a display unit 8. The processor 7 includes a CPU, memory, processing circuit, etc., and can be an information processor that is capable of different types of processing.

In FIG. 1A, the fiber bundle 3 is branched in the middle for providing two irradiating ends 3b and two second illuminating optical systems 5. However, the number of branch is not limited to two. Alternatively, no branch is made such that an irradiating end 3b may be adjacent to one side of the receiver 6.

Figure 2A:
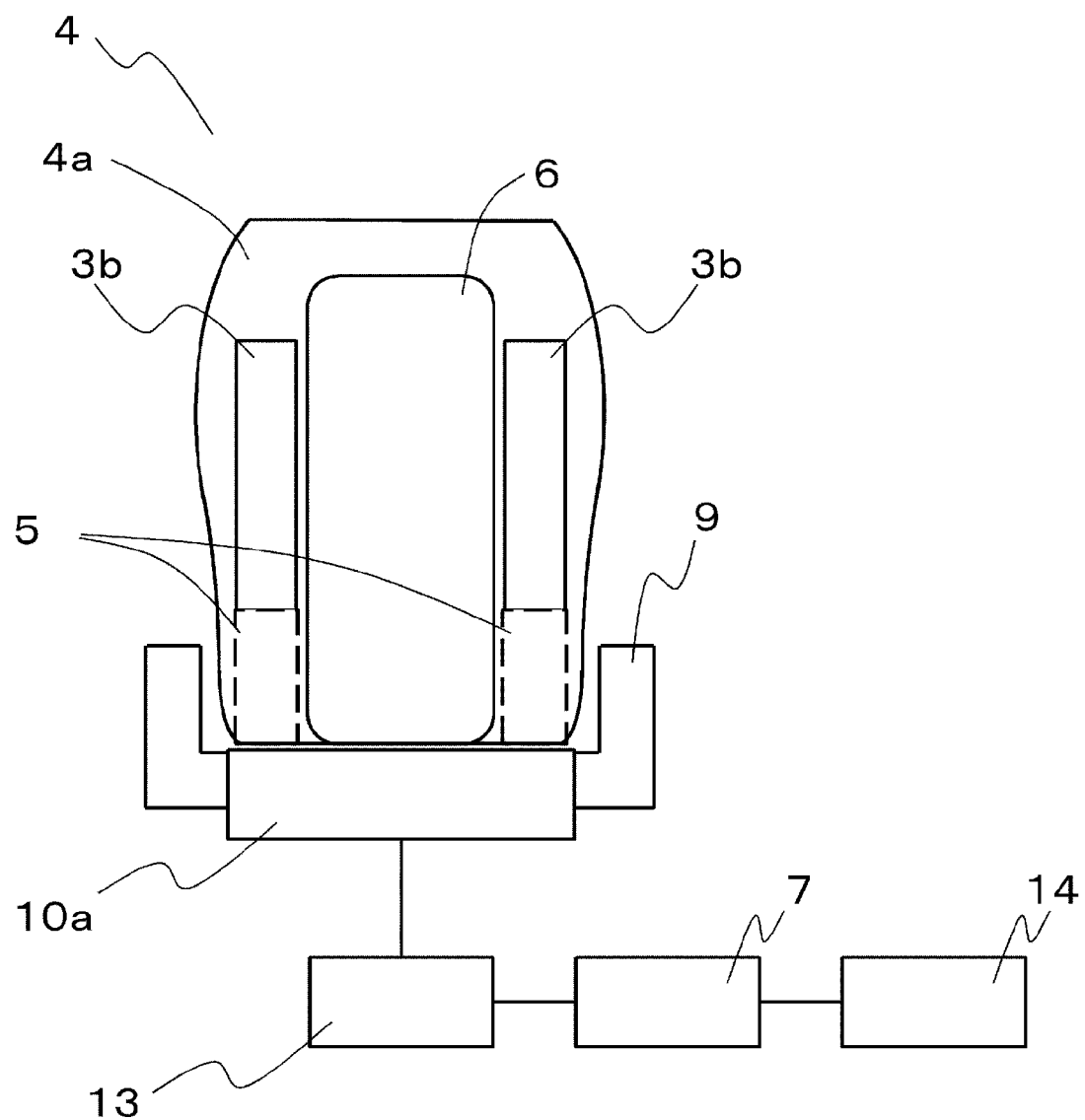
FIG. 2A is a view illustrating a photoacoustic probe of Example 1 of the invention.

Preferably, the photoacoustic probe 4 is covered with a housing 4a, as shown in FIG. 2A.

Preferably, a light source 1 emits near infrared light of a wavelength between about 600 nm to about 1,100 nm. For example, a pulse laser such as an Nd:YAG laser, alexandrite laser, or the like, is used. Also, a Ti:sa laser or OPO laser using Nd:YAG laser beams as excitation light may be used.

In FIG. 1A, light from the light source 1 was transmitted via a first illuminating optical system 2 and the fiber bundle 3. However, an optical transmission system is not limited thereto. For example, a mirror and a prism may be combined to yield reflection and refraction, which are used for transmission. The light source 1 may be a semiconductor laser to be placed at the irradiating end 3b.

Light emission and the receiving of photoacoustic waves by the receiver 6 must be synchronized. This can be achieved by branching any one of the paths between the light source 1 and the second illuminating optical system(s) 5 and providing a sensor (not shown), for example, a photodiode, for detection. With a detection signal as a trigger, the receiver 6 can initiate receiving. Otherwise, a pulse generator (not shown) may be used for synchronizing the illumination timing of the light source 1 and the receiving timing of the processor 7.

A photoacoustic apparatus 100 includes a light quantity meter 10 for measuring the quantity of light emitted from the irradiating end of the photoacoustic probe 4. The light quantity meter 10 can be photovoltaics such as a photodiode or a heat exchange power meter such as a thermopile.

Alternatively, light emitted from the irradiating end of the photoacoustic probe 4 may be diffused by a diffuser plate, and the diffused light may be captured by an infrared camera. In this case, the light quantity can be calculated based on the brightness values of the pixels of the infrared camera.

Because the photoacoustic probe 4 is tethered by a cable or the fiber bundle 3, its movable range is limited. Therefore, it is preferable that the light quantity meter 10 is located within a movable range of the photoacoustic probe 4. Alternatively, if the light quantity meter 10 is located outside of the movable range of the photoacoustic probe 4, the light quantity meter 10 is placed on a wagon or case (not shown) to be transferred into a movable range during measurement of light quantity.

An irradiation switch 19 is provided so that light can be emitted when the irradiating end of the photoacoustic probe 4 is opposed to the light quantity meter 10. When the irradiation switch 19 is pressed, a controller 17 executes control to set irradiating conditions. In a state that the irradiating conditions are set, an inner shutter of the light source 1 and a shutter 2c in the first optical system 2 are open. In a case the light source 1 is a Q-switched laser, a Q switch is switched on. Thus, light is emitted from the irradiating end of the photoacoustic probe 4.

The irradiation switch 19 may be a manual switch or foot switch that can be pressed directly by an operator. Alternatively, as shown in the drawing by a dotted line, the irradiation switch 19 may be provided near the light quantity meter 10 so that when the irradiating end of the photoacoustic probe 4 is opposed to the light quantity meter 10, the switch can be pressed.

A light quantity (Q) measured by the light quantity meter 10 is stored in a memory 13. The processor 7 determines whether the light quantity stored in the memory 13 is within a reference range or not; when the light quantity is above the reference range, "anomalous" is presented on a presentation unit 14. FIG. 1B shows a flow for the above situation. First, an operator directs the irradiating end of the photoacoustic probe 4 opposite to the light quantity meter 10. Subsequently, the operator presses an irradiation switch 19.

S11: The photoacoustic apparatus 100 sets irradiating conditions. That is, the inner shutter in the light source 1 and the shutter 2c in the first optical system 2 are open, or a Q switch is switched on if the light source 1 is a Q-switched laser, and light is emitted. The quantity of light emitted from the irradiating end of the photoacoustic probe 4 is measured by the light quantity meter 10, and the light quantity measured is stored in the memory 13.

S12: A difference from a reference light quantity is determined.

S13: When the difference in S12 is within a reference range, the procedure is terminated as "normal completion".

S14: When the difference in S12 is outside of the reference range, the procedure is terminated as "anomalous completion" ("abnormal completion").

In this flow, provided a reference value is 50 mJ for the total quantity of light emitted from the irradiating end of the photoacoustic probe 4, for example, a measurement value that falls within a range of 50 mJ±5 mJ is considered a normal completion. It should be noted that the reference value of total light quantity (50 mJ) and range (±5 mJ) are non-limiting examples. In S12, the memory 13 can store not only a specified reference value but also a history of previous light quantity data for comparison. The history of measurement value can include an immediate previous measurement value, an average of a plurality of previous measurement values, and a measurement value that has undergone statistic processing such as clearing outliers.

The presentation unit 14 may be an LED for indicating a status by lighting or flashing and/or a unit for voice notification. Alternatively, a display unit 8 may be used as a presentation unit 14 for indicating a status by letters and/or images.

FIG. 1A shows two processors 7: one for generating images, and the other for determining whether or not a light quantity is normal. However, only one processor 7 can perform both operations.

According to the above configuration, quantity changes in light emitted from the photoacoustic probe 4 can be detected immediately. Thus, faulty photoacoustic measurements due to unnoticed failure of an optical transmission system can be reduced. Consequently, the accuracy of measured light quantities and values of optical properties calculated using the light quantities will improve, whereby reliable photoacoustic data becomes available.

In the above description, photoacoustic measurement was used as an example. However, applications of the invention are not limited thereto. For example, the invention can be used for optical imaging techniques where a relatively high energy density is used, such as diffuse optical imaging (DOI). The same holds true for the following Examples.

Example 1

A light quantity meter 10 will now be described in detail with reference to FIGS. 2A to 2C.

In FIG. 2A, a holder 9 is provided for holding a photoacoustic probe 4 therein. A light quantity meter 10 is disposed in a position so as to oppose an irradiating end of the photoacoustic probe 4 in the holder 9. The purpose of this is to reduce an adverse effect when the photoacoustic probe 4 is held by an operator during measurement of light quantity, that is, the accuracy of the measurement may be lowered affected by movement of the operator. Further, the adverse effect may be completely eliminated if the operator puts the photoacoustic probe 4 in the holder 9 instead of holding it oneself and uses a switch positioned away from the photoacoustic probe to irradiate light.

In FIG. 2A, a light quantity meter 10 is shown in the form of a power meter 10a. The power meter 10a can be a photovoltaic or heat exchanging type, as described above. The power meter 10a measures the total quantity of light emitted from an irradiating end of a photoacoustic probe 4. A processor 7 compares the measured total light quantity with a reference value (or a previous measurement value) to determine whether the difference is within a predetermined range or not, and has a presentation unit 14 present the result presented thereon. Thus, the total quantity of light emitted from the irradiating end of the photoacoustic probe 4 can be measured comprehensively by the power meter 10a opposite to the irradiating end of the photoacoustic probe 4.

Figure 2B:
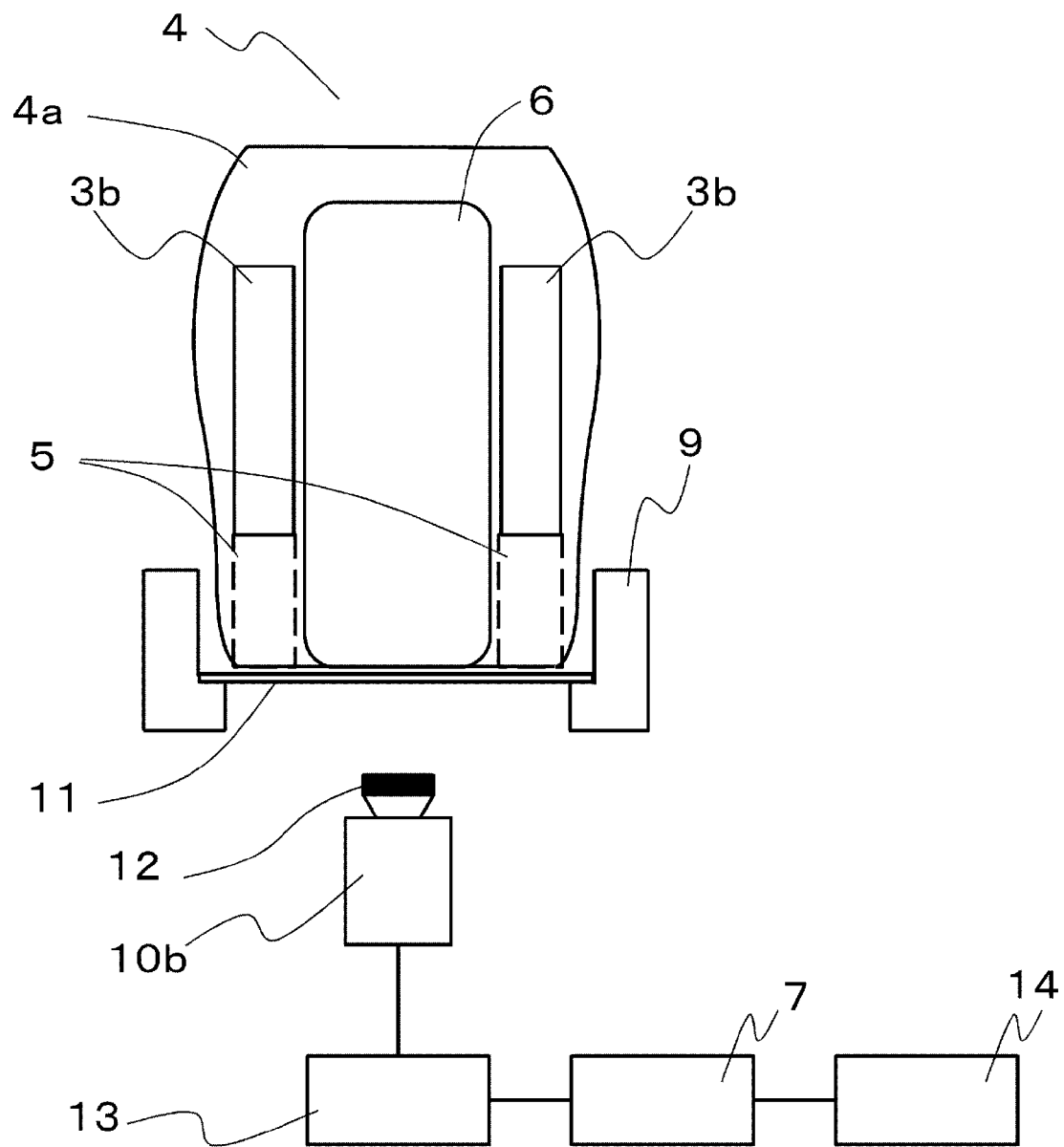
FIG. 2B is a view illustrating the photoacoustic probe of Example 1 of the invention.

Turning now to FIG. 2B, a light quantity meter 10 is shown in the form of an infrared camera 10b. However, it is difficult for the infrared camera 10b to directly capture light emitted from an irradiating end of a photoacoustic probe 4. To address this problem, a diffuser plate 11 is provided in a position opposite to the irradiating end of the photoacoustic probe 4, on which a focal point of the infrared camera 10b is adjusted.

Incidentally, intense light from the photoacoustic probe 4 can saturate the brightness values of pixels of an image captured by the infrared camera 10b, or can damage an image-receiving element of the infrared camera 10b. To avoid this, it is preferable that an ND filter 12 is provided between the diffuser plate 11 and the infrared camera 10b.

A sum of the brightness values of the pixels of an image captured by the infrared camera 10b is regarded the total quantity of light emitted from the irradiating end of the photoacoustic probe 4. A processor 7 compares this total light quantity with a reference value or the like to determine whether the difference is within a predetermined range or not, and has a presentation unit 14 present the result presented thereon.

The distribution of the brightness values of the pixels of an image captured by the infrared camera 10b represents the distribution of the quantity of light emitted from the irradiating end of the photoacoustic probe 4, that is, the distribution of the quantity of light irradiating the surface of an object. Thus, the processor 7 can use the light quantity distribution to determine the status of the light in terms of whether or not it is within a predetermined range. Here, the processor 7 can perform determination based on the brightness values of the pixels, an extract of any pixels, or an average of the brightness values in any pixel zone.

The use of light quantity distribution appreciates the benefit of keeping track of the status of light emission using the total light quantity as described above, and further improves the precision of photoacoustic measurement. This effect will now be described.

A level of intensity (or an initial sound pressure p) of photoacoustic waves of light, which is irradiated on the surface of an object and which enters the object while scattering, is expressed by the following expression (1):

$$p = \Gamma \mu_a \varphi \tag{1}$$

where φ denotes a light quantity, $\mu_a$ denotes an absorption coefficient of living tissue, and Γ denotes the Gruneisen parameter.

Thus, to determine an absorption coefficient $\mu_a$ of living tissue, data received at the receiver 6 corresponding the sound pressure p, the Gruneisen parameter of about 0.5, and a light quantity φ within the organism are required. The light quantity φ within the organism is calculated, with the light quantity distribution on the object's surface being a boundary condition, using a diffusion equation (transport equation) or the Monte Carlo method using known or estimated equivalent damping coefficient $\mu_{eff}$ within the organism. If the configuration includes the infrared camera 10b, the light quantity φ within the organism is calculated on a high precision basis, because the light quantity distribution of the light emitted from the irradiating end of the photoacoustic probe 4 or the light quantity distribution on the object's surface as the boundary condition is available.

Preferably, the processor 7 is capable of calibrating the brightness values of the infrared camera 10b. In calibration, the total quantity of light emitted from the irradiating end of the photoacoustic probe 4 is pre-measured by, for example, a power meter, and the value is compared with a sum of brightness values measured by the infrared camera 10b. Thus, a light quantity per brightness gradation can be calculated. For example, provided that a pixel's brightness gradation has 256 levels, brightness values of 1280×960 pixels are added up.

Next, still another example of a light quantity meter 10 will be described with reference to FIG. 2C. The power meter 10a in FIG. 2A has a large area so that the power meter 10a can face the entire irradiating end of the photoacoustic probe 4. In contrast, in FIG. 2C, a power meter 10a has a smaller area, and is scanned. For scanning, the power meter 10a with a smaller area is mounted on an XY stage 15. In this way, without a need for using an infrared camera 10b, the relatively inexpensive power meter 10a with a smaller area is capable of measuring the light quantity distribution within an irradiated plane shone by light from an irradiating end of a photoacoustic probe 4.

In accordance with ANSI Standard Z136.1-2000, a method for determining whether or not the irradiance energy per unit area exceeds the maximum permissible exposure (MPE) level for skin should use a spot size of a 3.5 mm beam diameter. Thus, the measurement area for the power meter 10a has a diameter of 3.5 mm, or an aperture 10c with a diameter of 3.5 mm is disposed on the power meter 10a, such that measurement is performed as per ANSI Standard Z136.1-2000 in terms of the irradiance energy per unit area.

A processor 7 determines whether or not an energy density measured by the power meter 10a exceeds a predetermined value to ensure safety of skin. The predetermined value employed was about 0.8 times the MPE level for skin taking a safety factor into consideration. When the processor 7 determines that an irradiance energy density has exceeded the predetermined value, the illuminating intensity of a light source 1 is adjusted to be lower (adjusting instruction ADJ). In this way, the light energy density is kept at or below the predetermined value so that safety is ensured.

Other ways to keep the light energy density at or below the MPE level include inserting a filter at some point between the light source 1 and the irradiating end of the photoacoustic probe 4, or inserting a diffuser plate with a large diffusing angle into a second illuminating optical system 5.

Figure 2C:
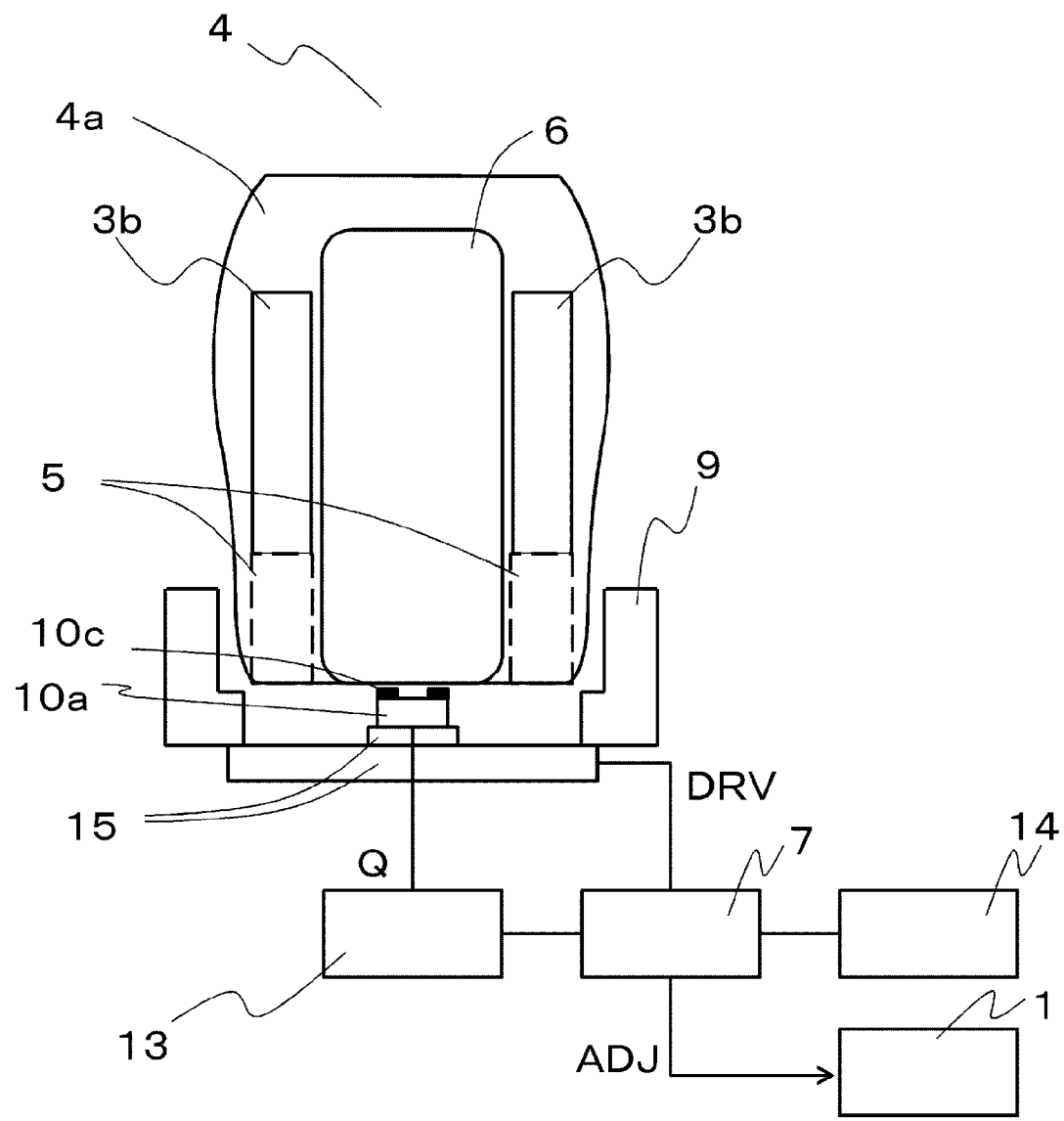
FIG. 2C is a view illustrating the photoacoustic probe of Example 1 of the invention.

The XY stage 15 shown in FIG. 2C was provided for the scanning of the power meter 10a. The XY stage 15 is operated by a drive instruction (DRV) from the processor 7. However, a scanning mechanism is not limited to this configuration. For example, to the contrary to the above description, the photoacoustic probe 4 held in a holder 9 may be scanned. That is, it is essential only that a measuring plane of the power meter 10a is scanned relative to the in-plane direction of the irradiating end of the photoacoustic probe 4.

In FIG. 2C, the compact power meter 10a was scanned to measure the light quantity distribution within a plane shone by light from the irradiating end of the photoacoustic probe 4. On the basis of the light quantity distribution, the processor 7 determines whether or not the light energy density is within a predetermined range, and has the result presented on a presentation unit 14. The processor 7 may determine changes in light quantity distribution based on the brightness values of the pixels, or by averaging only arbitrary pixels or arbitrary pixel zone.

This configuration enables not only safe measurement of total light quantity but also the computing of light quantity distribution within the object. In addition, the use of a relatively inexpensive power meter can lead to cost reduction.

Example 2

In Example 2, contents presented by a presentation unit 14 will be described.

Reduction of the quantity of light emitted from an irradiating end of a photoacoustic probe 4 can be ascribed to reduction of the quantity of light emission from a light source 1, and foreign body adherence to an optical element between a first illuminating optical system 2 and a second illuminating optical system 5, to an end face of a fiber bundle 3, and to the irradiating end of the photoacoustic probe 4.

As shown in FIG. 1A, a reflection element 2b and a photometer 2a for measuring its reflected light are provided in the first illuminating optical system 2 (or in the light source 1). The reflection element 2b is parallel-plate glass or a mirror that reflects a few percent of emitted light. The photometer 2a is a photodiode or photomultiplier tube for measuring reflected light. Thus, a reflected light quantity is monitored by the photometer 2a, such that decrease in emitted light quantity at the light source 1 is detected. In this case, the presentation unit 14 indicates a light quantity error and also indicates that maintenance is required for the light source 1.

Figure 3A:
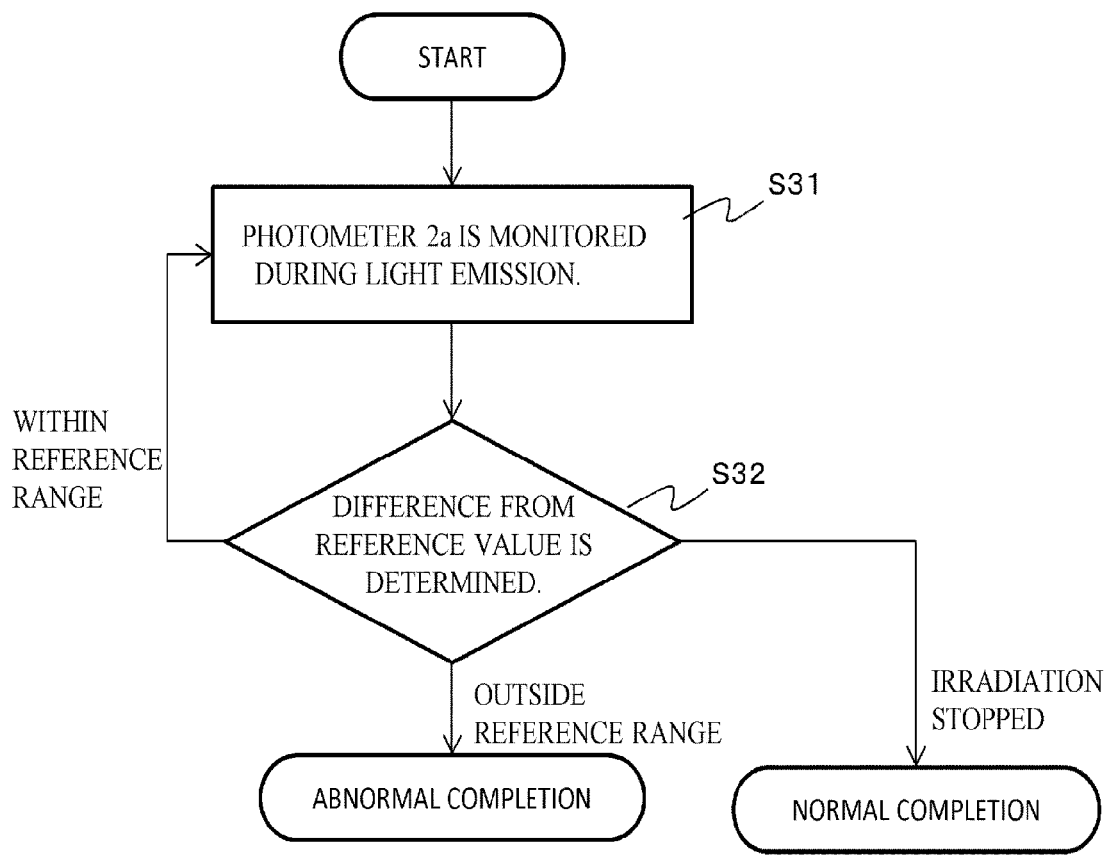
FIG. 3A is a flow chart illustrating operation in Example 2 of the invention.

FIG. 3A shows a flow of light emission.

S31: During light emission, the photometer 2a is monitored.

S32: The value indicated by the photometer 2a is compared with a reference value; if the resulting light quantity is within a reference range, the procedure returns to S31 during light emission. If the light quantity is outside the reference range, the procedure will be terminated as abnormal completion (S33). The photometer 2a measures reflected light from the reflection element 2b, which is only about a few percent of the original light; therefore, when an emitted light quantity at the light source 1 is 100 mJ, 5 mJ that is 5 percent of 100 mJ will be measured. Thus, a reference range for determination is 5±0.5 mJ. Note that the light quantities and percentage above are examples only, and do not intend to limit actual values thereto.

S33: In a case of abnormal completion, the presentation unit 14 indicates that maintenance is required for the light source 1. For safety reasons, maintenance of the light source 1 should not be performed by an operator, for example, a physician. Therefore, preferably, the indication in the step urges the operator to contact service personnel.

As for foreign body adherence between the first illuminating optical system 2 and the second illuminating optical system 5, such incident should occur less frequently because the path is usually covered. In case of a failure in the cover, it will be readily and visually checked from the exterior.

Foreign body adherence to the irradiating end of the photoacoustic probe 4 occurs more frequently. A major cause for this is sonar gel (acoustic matching gel) that is applied between the receiver 6 and the object during photoacoustic measurement. Foreign objects such as contaminants in the sonar gel and opaque matters that are dried leftovers of the sonar gel remaining on the irradiating end of the photoacoustic probe 4 become adherent.

Figure 3B:
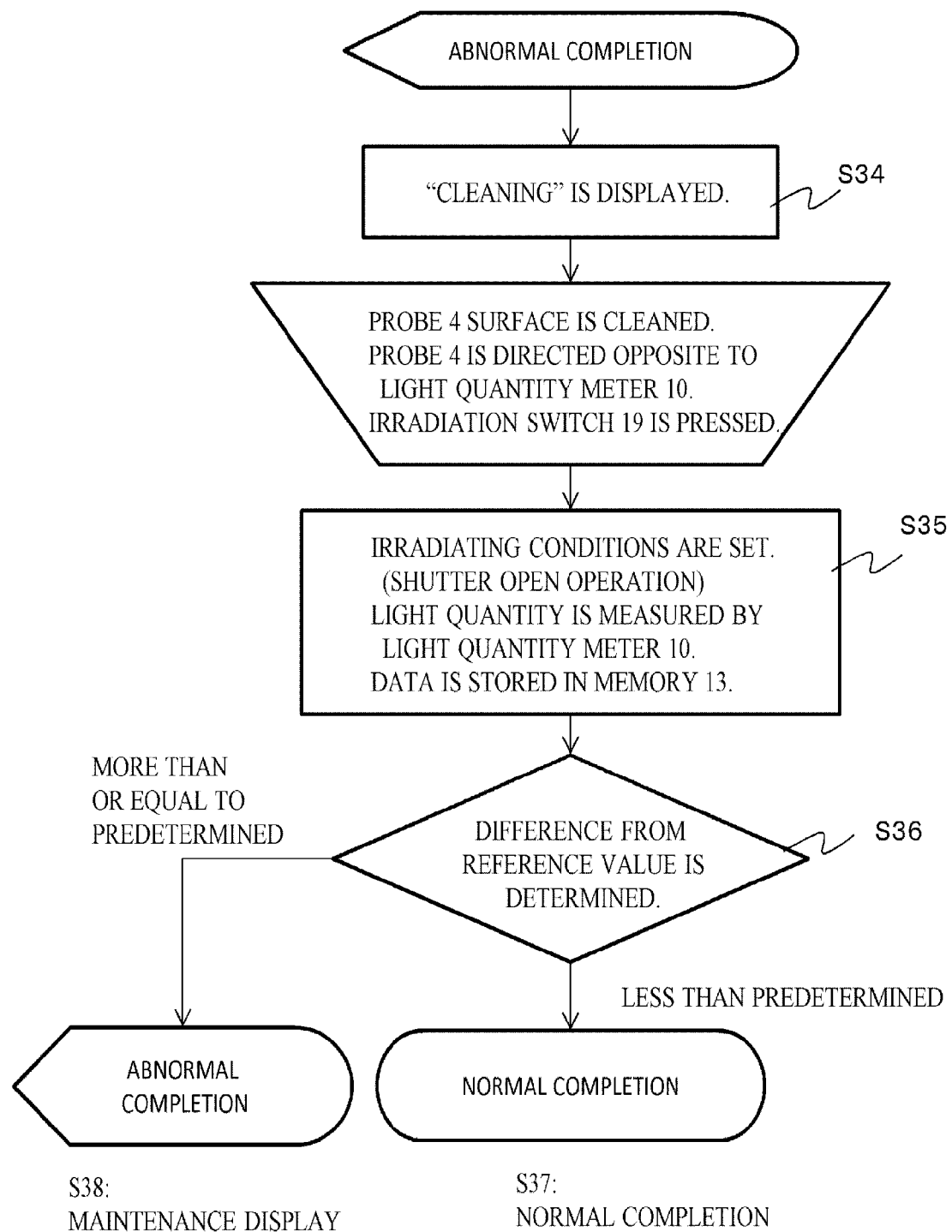
FIG. 3B is a flow chart illustrating the operation in Example 2 of the invention.

Thus, in a case of anomalous completion in the flow shown in FIG. 1B, preferably an operator is urged to clean. A flow in FIG. 3B depicts a procedure upon anomalous completion, which will be described as follows.

S34: A presentation unit 14 presents a message urging an operator to clean an irradiating end of a photoacoustic probe 4.

Checking the message, the operator cleans the irradiating end of the photoacoustic probe 4, directs the photoacoustic probe 4 opposite to a light quantity meter 10 again, and presses an irradiation switch 19.

S35: A photoacoustic apparatus 100 sets irradiating conditions. That is, an inner shutter (not shown) in a light source 1 and a shutter 2c in a first optical system 2 are open, or a Q switch is switched on if the light source 1 is a Q-switched laser, and light is emitted. The quantity of light emitted from the irradiating end of the photoacoustic probe 4 is measured by the light quantity meter 10, and the data is stored in a memory 13.

S36: A difference between a reference light quantity and a measurement value is determined.

S37: When the difference in S36 is within a reference range, the procedure is terminated as "normal completion".

S38: When the difference in S36 is outside of the reference range, "abnormal completion" is presented. This means that the light quantity change failed to recover to the reference range despite cleaning; therefore, the presentation unit 14 presents that maintenance is required. In this situation, foreign body adherence somewhere between the first illuminating optical system 2 and the second illuminating optical system 5, or displacement or damage in optical system(s) are highly likely, in which cases cause investigation and/or repairs can be difficult. Hence, rather than letting the operator, such as a physician, deal with trouble oneself, it is preferable to advise the operator through presentation to contact service personnel.

In S38, before presenting the abnormal completion message right away, the message urging cleaning may be presented once again by the presentation unit 14.

As described above, even though a total light quantity once turned out outside a normal range, a procedure as simple as cleaning the irradiating end of the photoacoustic probe 4 may work and enable good measurement. According to this Example, in the preceding situation, the operator is informed that a normal status may be restored by cleaning oneself without maintenance by professional; therefore, the operator has a chance to readily restore the light quantity within a reference range. As a result, the degree of capacity utilization of the photoacoustic apparatus 100 is improved.

Example 3

At an irradiating end of a photoacoustic probe 4, light with a relatively high energy in the range of several tens to a hundred and several tens mJ is emitted from a relatively small area. Even if the irradiance energy density does not exceed the MPE level for skin, as described in Example 1, it may exceed that for retina, which has a smaller reference value. Thus, for safety of the object and the operator, it is preferable to provide a mechanism near the irradiating end of the photoacoustic probe 4 to prohibit emission when not in contact with the object.

Figure 4A:
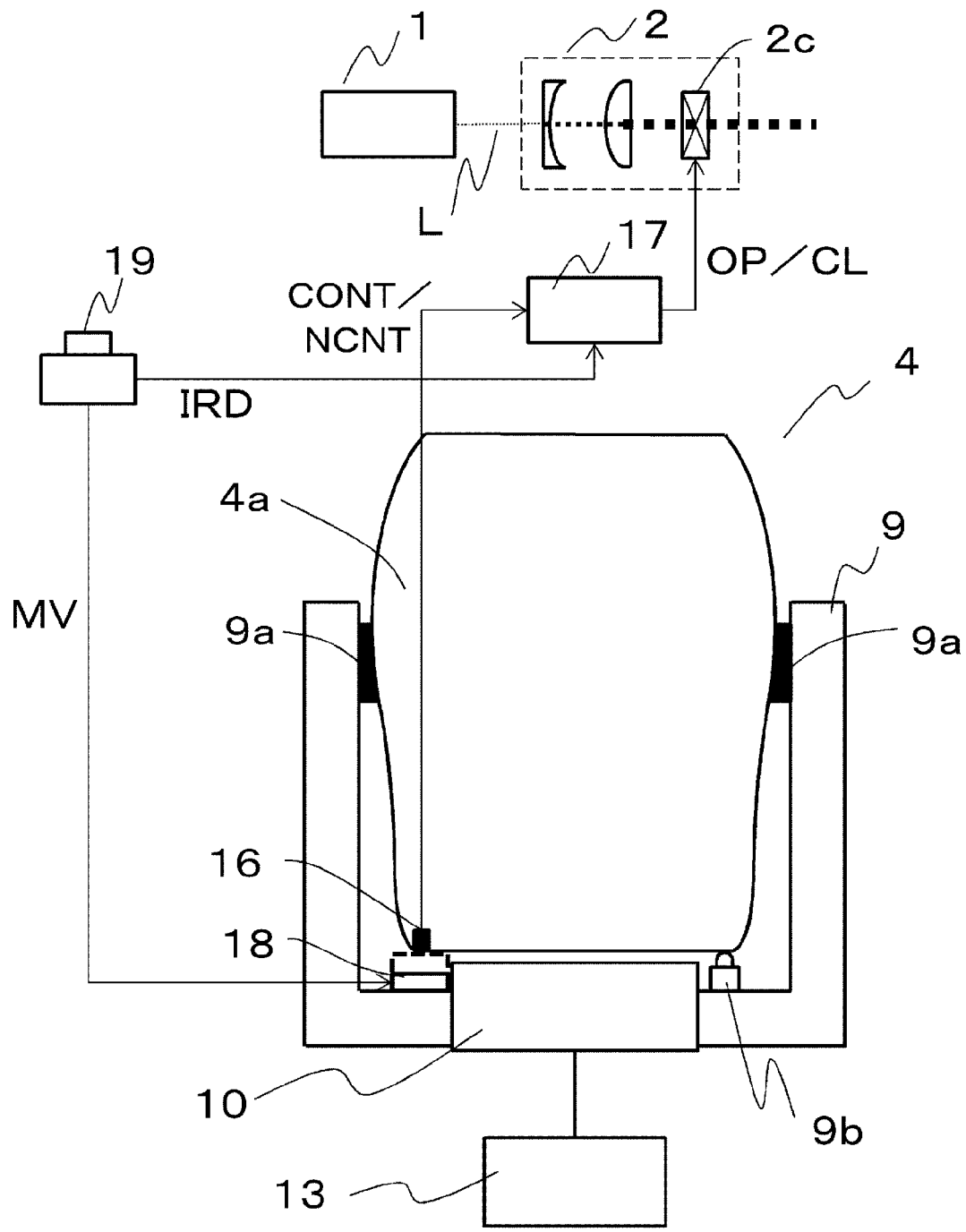
FIG. 4A is a view illustrating a photoacoustic probe of Example 3 of the invention.

In this Example, as shown in FIG. 4A, a contact sensor 16 for determining a contact status is provided outside the irradiating end of the photoacoustic probe 4. An optical, electrostatic or mechanical sensor, or a strain gauge may be used as the contact sensor 16. Alternatively, a receiver 6 (FIG. 1A) may determine contact by transmitting and receiving ultrasonic waves. The contact sensor 16 outputs contact information (CONT) when the irradiating end is in contact with an object and no-contact information (NCNT) when the irradiating end is not in contact with the object.

A controller 17 outputs a shutter open/close instruction (OP/CL) in accordance with the contact/no-contact information. That is, when the no-contact information is output, the controller 17 closes a shutter 2c in a first illuminating optical system 2 and an inner shutter (not shown) in a light source 1. In a case the light source 1 is a Q-switched laser, a Q switch is switched off by the controller 17. Thus, the controller 17 prevents light (L) from being emitted from the irradiating end of the photoacoustic probe 4.

In contrast, when the contact information is output, the controller 17 permits emission of light from the irradiating end of the photoacoustic probe 4. That is, the controller 17 opens the shutter 2c and the inner shutter in the light source 1, or switches on the Q switch if the light source 1 is a Q-switched laser.

The above configuration ensures safety when the probe is not in contact with an object. However, measurement of total light quantity according to the invention with a photoacoustic probe 4 being held in a holder 9 can have problems depending on the shape of the holder 9.

That is, the presence of a space (gap) in the holder 9 at a position opposing a contact sensor 16 causes an output of the no-contact information from the contact sensor 16. Consequently, when an operator presses the irradiation switch 19, the controller 17 does not permit light emission from the irradiating end of the photoacoustic probe 4. Hence, light is not emitted. As a result, a light quantity meter 10 provided in the holder 9 cannot perform measurement. Thus, when the holder 9 houses the photoacoustic probe 4 in a normal manner, it is necessary that the contact sensor 16 output the contact information. To this end, some examples of configuration and method will be described as follows.

In the first example, regardless of a gap in a holder 9 at a position opposing a contact sensor 16, light is forced to irradiate when an irradiation switch 19 is pressed. That is, when the irradiation switch 19 is pressed, an irradiation instruction (IRD) is output to a controller 17.

With the above configuration, however, the pressing of the irradiation switch 19 will cause light emission anyway, even when a photoacoustic probe 4 is not held in the holder 9 in a normal manner. Hence, it is preferable that the irradiation switch 19 is disposed adjacent to the holder 9 so as to draw attentions of an operator to make sure the photoacoustic probe 4 is in place in the holder 9.

Figure 4B:
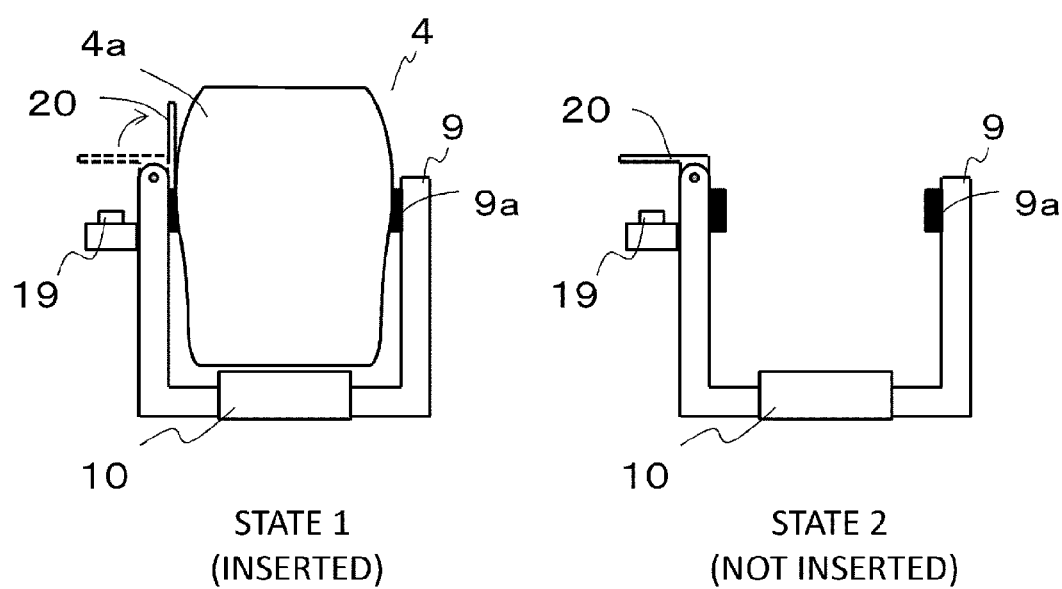
FIG. 4B is a view illustrating the photoacoustic probe of Example 3 of the invention.

Alternatively and more preferably, as shown in FIG. 4B, a cover 20 is provided, which enables operation of the irradiation switch 19 only when the photoacoustic probe 4 is in the holder 9, but disables operation when the photoacoustic probe 4 is not in the holder 9. When the photoacoustic probe 4 is in the holder 9, light emission is allowed only when the irradiation switch 19 is pressed.

In the next example, the gap between a contact sensor 16 and a position within a holder 9 opposing the contact sensor 16 is narrowed so that the contact sensor 16 can sense a contact status. For this method, the gap between a photoacoustic probe 4 and the holder 9 is filled with an elastic body 9a, and the shapes of the interior of the holder, a housing 4a of the probe, and the elastic body 9a are individually adjusted to shield light.

In this way, when the photoacoustic probe 4 is not held in place, the contact information is not output and light is not emitted. When the photoacoustic probe 4 is held in place, and when light is emitted, the leakage of light to the outside of the holder 9 is restricted because the elastic body 9a as a light shield fills the gap between the photoacoustic probe 4 and the holder 9.

In another example, as shown in FIG. 4A, a movable part 18 is provided in a holder 9 at a position opposing a contact sensor 16. The movable part 18 is moved to a position where the contact sensor 16 is capable of sensing a contact status when an irradiation switch 19 is pressed (movable part operation instruction MV). In this way, when the photoacoustic probe 4 is held in the holder 9, light emission is allowed only when the irradiation switch 19 is pressed.

With the above configurations and methods, light emission is enabled in a state in which the photoacoustic probe 4 is held in the holder 9 in a normal manner. As described above, the use of the light quantity meter 10 enables measurement of the total quantity of light emitted from the irradiating end of the photoacoustic probe 4.

In addition, a hold sensor 9b may be provided in the holder 9 or adjacent to the light quantity meter 10, which sensor outputs hold information to the controller 17 upon sensing that the photoacoustic probe 4 is held (accommodated) in the holder 9. Receiving the hold information, the controller 17 enables emission of light (for example, opens a shutter 2c). A mechanical, optical, or electrostatic switch may be used preferably for the hold sensor 9b.

In this way, the light quantity meter 10 can measure total light quantity only when the photoacoustic probe 4 is held in place in the holder 9 at a predetermined position. Additionally, by providing a plurality of hold sensors 9b, measurement of total light quantity is performed only when the irradiating end of the photoacoustic probe 4 and the light quantity meter is parallel, which contributes to reproduction of measurement conditions for the light quantity meter 10 and to improvement of the measurement accuracy.

The configurations and controlling methods described above may be used alone or in combination. Consequently, the irradiating end of the photoacoustic probe 4 is not allowed to emit light when not in contact with an object; thus, safety of the object and the operator is ensured. Conversely, when the photoacoustic probe 4 is held in place in the holder 9 at the predetermined position, light is emitted so as to enable light quantity measurement.

In FIG. 4A, an elastic body 9a was provided in an inner periphery of the holder 9 at a position that comes in contact with the photoacoustic probe 4. Deformable resin such as different kinds of rubber and urethane is preferably used for the elastic body 9a. The body of the holder 9 was formed from relatively rigid materials such as metals, resin such as plastic, or ceramics. By providing the elastic body 9a, the gap between the photoacoustic probe 4 and the holder 9 is filled when the photoacoustic probe 4 is held in the holder 9. In this way, the leakage of light to the exterior of the holder 9 can be decreased while the quantity of light emitted from the irradiating end of the photoacoustic probe 4 is being measured by the light quantity meter 10. As a result, object and operator safety is improved.

Figure 4C:
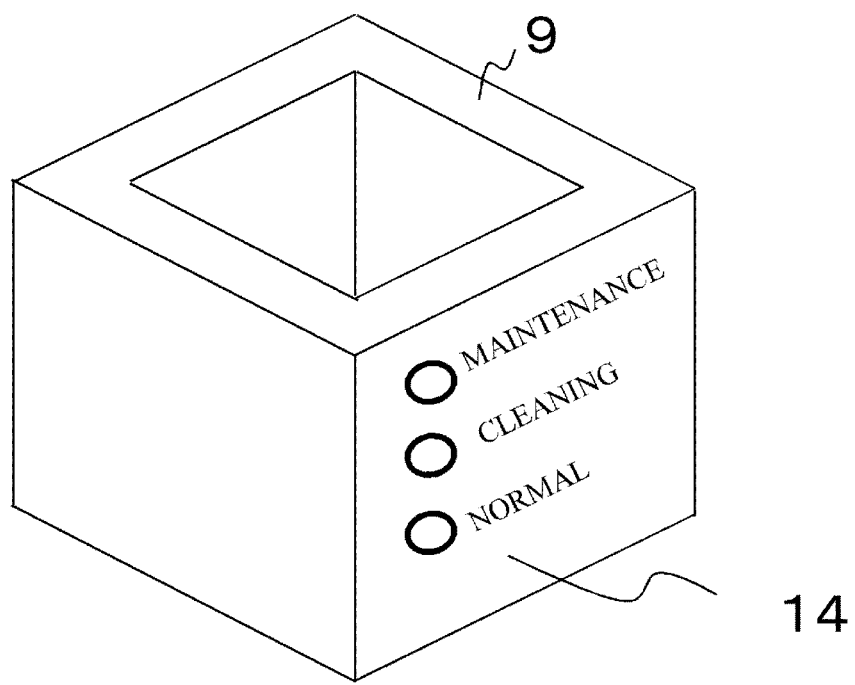
FIG. 4C is a view illustrating a presentation unit of Example 3 of the invention.

In this Example, the presentation unit 14 is provided on a side of the holder 9. FIG. 4C exemplifies a presentation unit 14 including an LED for indicating contents to be presented for an operator. The operator is notified by lighting or flashing of the LED.

Figure 4D:
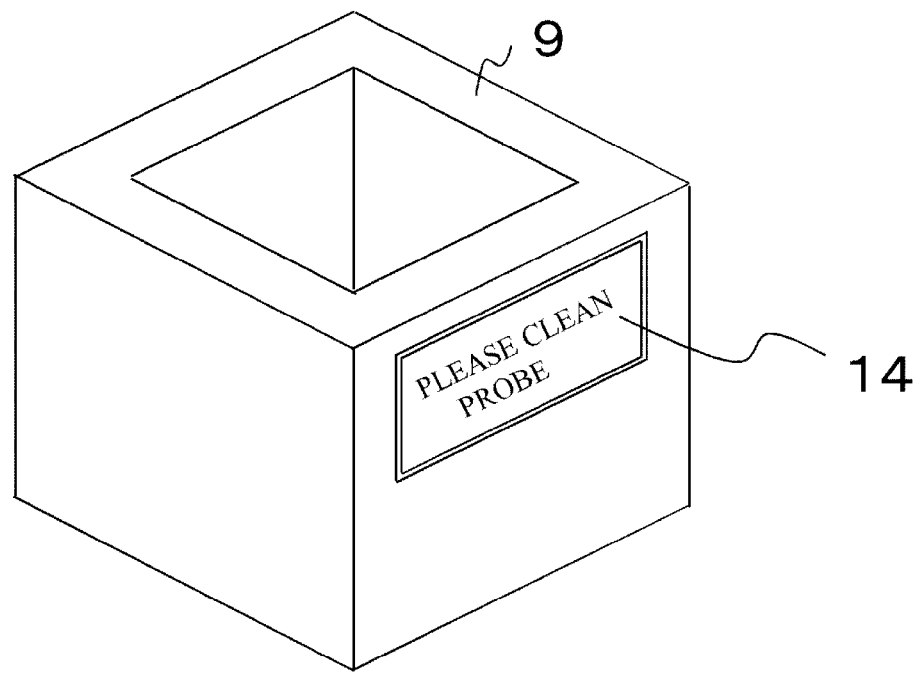
FIG. 4D is a view illustrating the presentation unit of Example 3 of the invention.

In FIG. 4D, a presentation unit 14 is provided with a liquid crystal monitor, on which contents to be presented for an operator are expressed in letters. These methods facilitate an operator to understand the status of the apparatus and instructions for the operator.

Example 4

Figure 5:
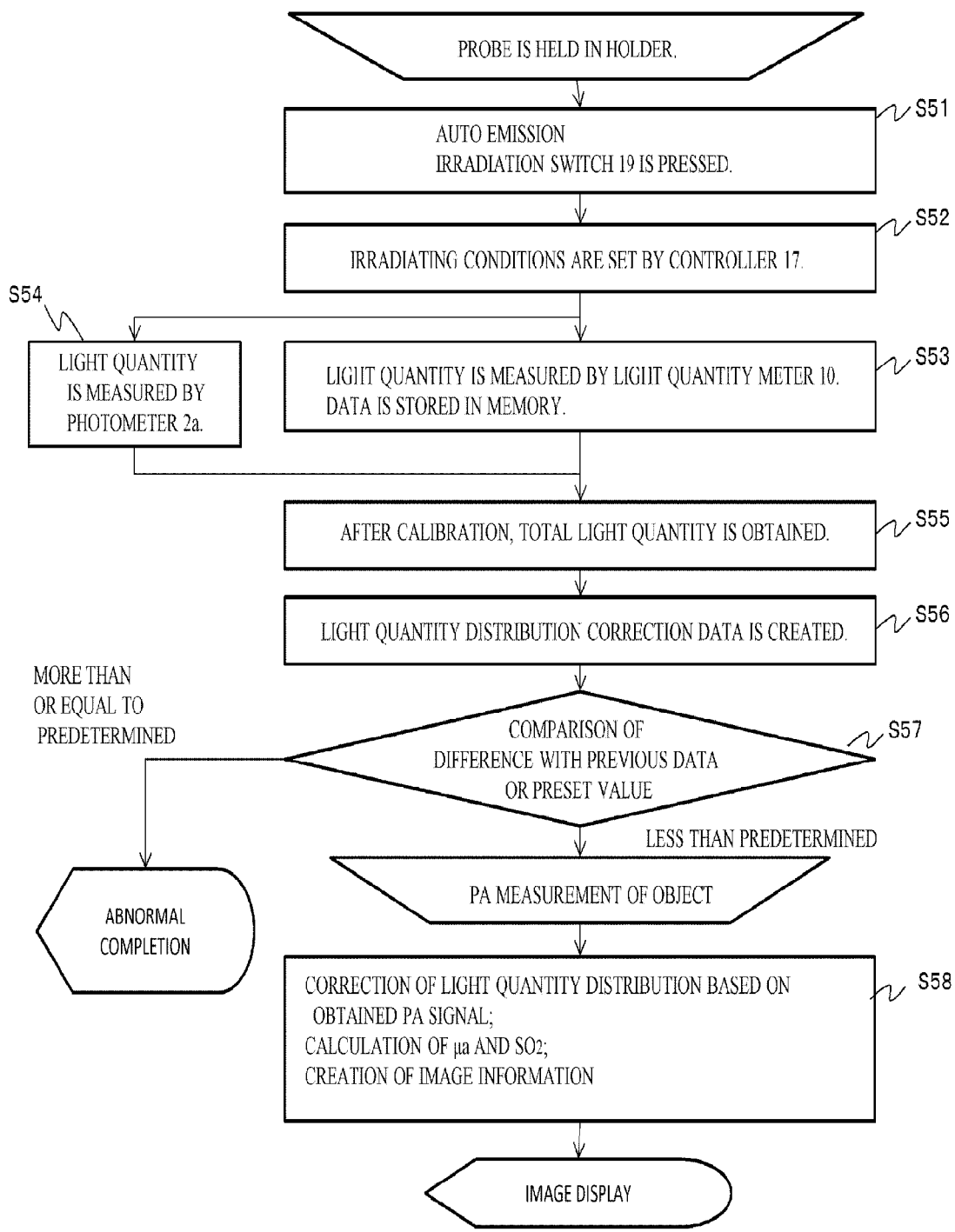
FIG. 5 is a flow chart illustrating operation in Example 4 of the invention.

With reference to a flow chart in FIG. 5, directions for use of a photoacoustic apparatus 100 including a photoacoustic probe 4 and a holder 9 will be described. In this Example, an infrared camera 10b, such as the one shown in FIG. 2B, was used as a light quantity meter 10.

At start-up of the apparatus or during standby, the photoacoustic probe 4 is held in the holder 9.

S51: At start-up of the apparatus, a controller 17 performs a sequence of auto-emission. Alternatively, during standby, when an operator places the photoacoustic probe 4 in the holder 9 and presses an irradiation switch 19, the controller 17 performs a sequence for emission (S52).

S52: If the photoacoustic probe 4 is provided with a contact sensor 16, the contact sensor 16 is made ready to sense a contact status. For example, a movable part 18 is moved as shown in FIG. 4A. The controller 17 sets irradiating conditions. If the holder 9 has a hold sensor 9b therein, the controller 17 sets irradiating conditions after the hold sensor 9b sensed the photoacoustic probe 4. If neither of the contact sensor 16 and the hold sensor 9b is present, the controller 17 sets irradiating conditions after S51.

Here, the irradiating conditions set by the controller 17 includes opening an inner shutter in a light source 1 and a shutter in a first optical system 2, or switching on a Q switch if the light source 1 is a Q-switched laser. Thus, light is emitted from the irradiating end of the photoacoustic probe 4. The duration and the number of times of irradiation are programmed in the controller 17; in this Example, irradiation was executed 100 times (10 sec×10 Hz).

S53: Light emitted from the irradiating end of the photoacoustic probe 4 is diffused by a diffuser plate 11 to be captured by the infrared camera 10b. The brightness values of pixels of the infrared camera 10b are stored in a memory 13.

S54: Concurrent with S53, a photometer 2a provided in a second optical system 2 (FIG. 1A) measures the emitted light. It is intended that the photometer 2a has already undergone calibration for converting total light quantity.

The calibration takes advantage of the direct proportional relation between a light quantity measured by the photometer 2a and a total light quantity from the irradiating end of the photoacoustic probe 4. That is, using a total light quantity measured by the light quantity meter 10 in FIG. 1A and the then light quantity detected by the photometer 2a, calibration is performed in advance for creating a conversion expression.

S55: A processor 7 calculates a sum of the brightness values of the pixels of the image captured in S53, and executes calibration of the brightness values using the calculated sum and the measurement value provided by the photometer 2a in S54. This enables the brightness for imaging by the infrared camera 10b to be calibrated, whereby a light quantity can be derived from the brightness values. Using the brightness values of the photometer 2a or infrared camera 10a, the total quantity of light emitted from the irradiating end of the photoacoustic probe 4 is obtained.

S56: The processor 7 computes a boundary condition based on the total light quantity obtained in S55 and an irradiated area of the object, or based on the light quantity distribution on the object's surface established using the calibrated brightness values. Using this boundary condition, the distribution of the quantity of light entering the object as scattering and being absorbed is calculated, and light quantity distribution correction data is created.

S57: Any of the total light quantity data, brightness data, and light quantity distribution data within organism is compared with corresponding previous data or a preset reference value. In this Example, a preset value for a total light quantity was 50 mJ and a predetermined reference range was 50±5 mJ. When a difference exceeds the predetermined value, in other words, when the total light quantity is 45 mJ or less or 55 mJ or more, "anomalous completion" (abnormal completion) is determined and indicated on either a presentation unit 14 or a display unit 8.

In a case where a decrease in total light quantity is exhibited, such a change in the total light quantity may be ascribed to contamination of the irradiating end of the photoacoustic probe 4 or diffuser plate 11 (light quantity meter 10); therefore, the presented message at this point will contain the wording "clean and resume" to call attentions. To resume measurement, it is instructed to return to S51. It is also possible that optical transmission, such as the light source 1 and/or a fiber bundle 3 has trouble; therefore, if there is no improvement after measurement is resumed, "abnormal completion" is determined.

If the difference is less than predetermined, the operator holds the photoacoustic probe 4 and performs photoacoustic measurement of the object. Thus, variations in total light quantity or brightness data that is derived from the total light quantity, or in light quantity distribution data within organism can be minimized; therefore, stable photoacoustic measurement data becomes available.

S58: A photoacoustic image is created based on obtained photoacoustic signals, which image is displayed on the display unit 8. The total light quantity when the photoacoustic signals were obtained is converted based on the measurement value provided by the photometer 2a. Using the converted total light quantity and the light quantity distribution correction data from S56, the light quantity distribution within the object when the photoacoustic signals were obtained is corrected and established.

As described above, photoacoustic is expressed by the following expression (1):

$$p = \Gamma \mu_a \varphi \quad (1)$$

where p denotes a photoacoustic initial sound pressure, $\Gamma$ denotes the Gruneisen parameter, $\mu_a$ denotes an absorption coefficient, and $\varphi$ denotes a light quantity. The absorption coefficient $\mu_a$ can be determined from the photoacoustic signal (p), the corrected light quantity distribution within object ($\varphi$), and the Gruneisen parameter $\Gamma$ of about 0.5.

Further, by varying the wavelength of light from the light source 1, spectral characteristics of an absorber as a photoacoustic sound source can be figured out. For example, when blood (hemoglobin) is an absorber, an oxygen saturation level of hemoglobin is measurable. Consequently, it becomes possible to measure precisely the light quantity distribution on the object's surface, which is a boundary condition used for precise measurement of light quantity distribution within the object. This leads to improved measuring performance of absorption coefficient $\mu_a$ and oxygen saturation level.

The above-mentioned flow is also usable when a power meter 10a is used as a light quantity meter 10. Here, when the power meter 10a itself has been calibrated, the calibration procedure for the light quantity meter 10 described in S55 is unnecessary; the photometer 2a can be calibrated as is described in Example 1, as with S54.

Example 5

Figure 6:
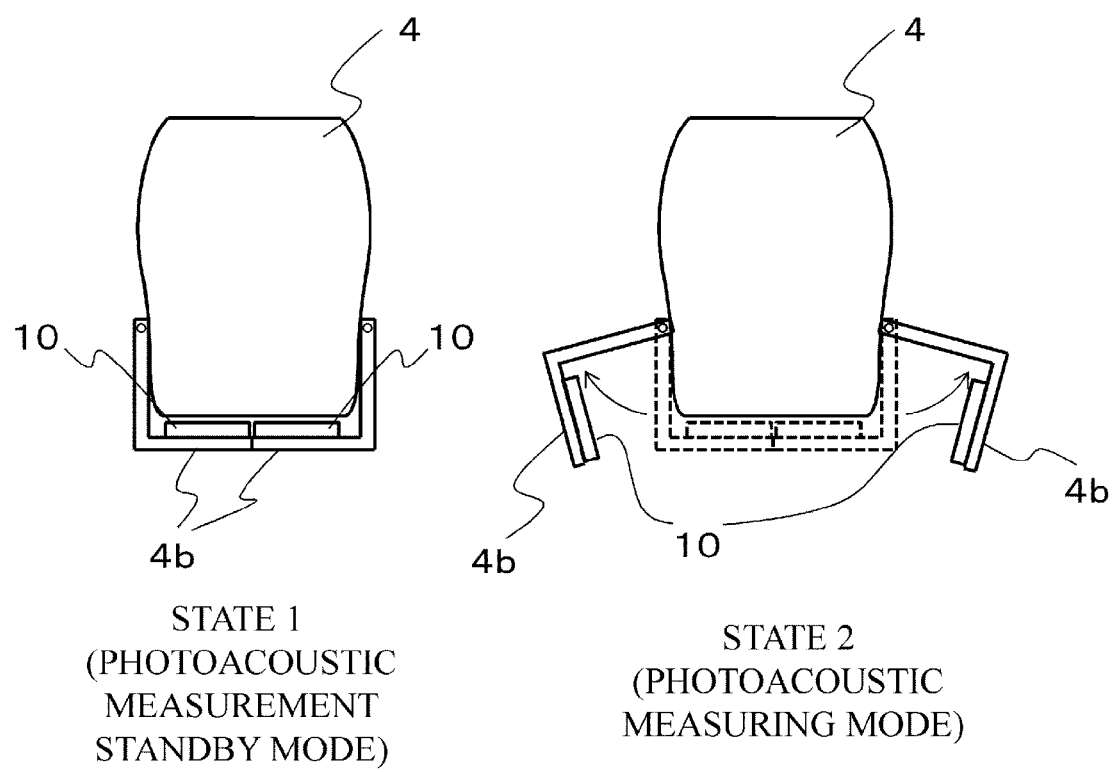
FIG. 6 is a view illustrating a photoacoustic probe of Example 5 of the invention.
Figure 7:
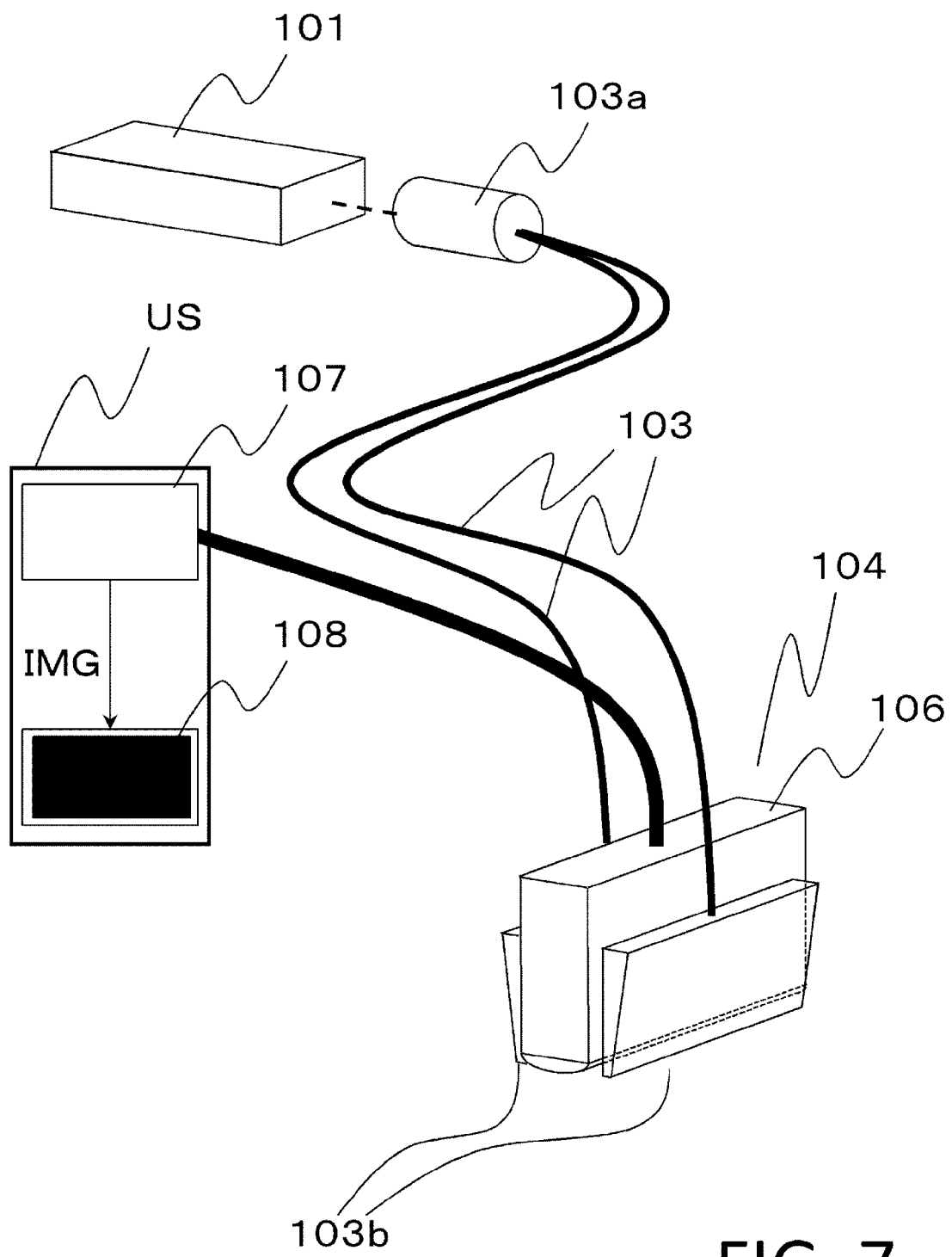
FIG. 7 is a view illustrating a configuration of a photoacoustic apparatus of the background art.

In Example 5, a light quantity meter 10 is provided for a photoacoustic probe 4. In FIG. 6, in a state 1 (photoacoustic measurement standby mode), a probe cover 4b covers an irradiating end of the photoacoustic probe 4, while in a state 2 (photoacoustic measuring mode), the probe cover 4b split opens. Thus, measurement can be performed while the cover is open. A light quantity meter 10 is provided inside the probe cover 4b, or at the irradiating end side of the photoacoustic probe 4.

With such configuration, the photoacoustic probe 4 and the light quantity meter 10 can be combined into a single unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-204513, filed on Sep. 30, 2013, which is hereby incorporated by reference herein in its entirety.

What is claimed is:

1. An object information acquiring apparatus comprising:
an optical transmission system for transmitting light from a light source; a photoacoustic probe including an irradiating end for irradiating an object with the light and a receiver for receiving acoustic waves generated by the object that has been irradiated with the light;
a processor for acquiring information on the object based on the acoustic waves;
a light quantity meter removably positioned facing the irradiating end, for measuring a quantity of light emitted from the irradiating end prior to irradiating the object with the light by acquiring a total quantity of light or a light quantity distribution within a plane irradiated by the light;
a memory for storing a measurement value measured by the light quantity meter; and
a presentation unit,
wherein the processor is configured to compare the measurement value with a reference value of light quantity or a history of measurement value stored in the memory to determine whether or not the measurement value is within a reference range, and cause the presentation unit to present a result of the determination thereon,
the processor is configured to, when a difference between the measurement value and the reference value of light quantity or the history of measurement value stored in the memory is larger than a predetermined value, cause the presentation unit to present thereon an indication to the effect that the measurement value is anomalous, and when the difference is less than the predetermined value, the processor enables photoacoustic measurement of the object.

2. The object information acquiring apparatus according to claim 1, further comprising:
   an irradiation switch enabling an operator to direct light emission; and
   a controller for setting irradiation conditions such that light is emitted from the irradiating end when the irradiation switch is pressed.

3. The object information acquiring apparatus according to claim 1, wherein the processor is configured to provide an indication urging to perform maintenance of the object information acquiring apparatus to the presentation unit when providing the indication that the measurement value is anomalous.

4. The object information acquiring apparatus according to claim 3, wherein the maintenance is cleaning of the irradiating end.

5. The object information acquiring apparatus according to claim 1, wherein the light quantity meter is a power meter.

6. The object information acquiring apparatus according to claim 1, further comprising:
   a diffuser plate for diffusing light emitted from the irradiating end, wherein
   the light quantity meter is an infrared camera for capturing light diffused by the diffuser plate, and
   the processor is configured to compute at least one of a total quantity of light emitted from the irradiating end and a light quantity distribution within a plane shone by the light, on the basis of brightness values of pixels obtained from the infrared camera imaging.

7. The object information acquiring apparatus according to claim 6, wherein the processor is configured to perform calibration to convert the brightness values of the pixels of the infrared camera into a total quantity of light emitted from the irradiating end.

8. The object information acquiring apparatus according to claim 1, further comprising a stage on which the light quantity meter and the irradiating end are scanned relative to each other.

9. The object information acquiring apparatus according to claim 1, wherein the processor is configured to lower an energy density of light emitted from the irradiating end when the energy density of light emitted from the irradiating end exceeds a predetermined value.

10. The object information acquiring apparatus according to claim 1, further comprising a holder for holding the photoacoustic probe.

11. The object information acquiring apparatus according to claim 10, wherein the holder has an elastic body for shielding light while holding the photoacoustic probe.

12. The object information acquiring apparatus according to claim 10, further comprising a cover for disabling operation of the irradiation switch operated by an operator directing light emission in a state in which the holder is not holding the photoacoustic probe and for enabling the operation of the irradiation switch in a state where the holder is holding the photoacoustic probe.

13. The object information acquiring apparatus according to claim 12, wherein the photoacoustic probe has a contact sensor for sensing whether or not the photoacoustic probe is in contact with the object, and
   wherein the object information acquiring apparatus further comprises:
   a controller for causing the contact sensor to determine a contact status when the irradiation switch is pressed.

14. The object information acquiring apparatus according to claim 13, further comprising a movable part disposed inside the holder at a position opposing the contact sensor when the photoacoustic probe is held in the holder,
   wherein the processor is configured to, when the irradiation switch is pressed, move the movable part to a position at which the contact sensor can detect a contact status.

15. The object information acquiring apparatus according to claim 13, wherein the holder has a hold sensor for sensing whether or not the photoacoustic probe is held in the holder, and
   wherein the controller sets light irradiating conditions to emit light from the irradiating end when the hold sensor has sensed that the photoacoustic probe is held in the holder.

16. The object information acquiring apparatus according to claim 1, further comprising a display unit for displaying information on the object.

17. The object information acquiring apparatus according to claim 16, wherein the presentation unit is the display unit.

18. The object information acquiring apparatus according to claim 1, wherein the presentation unit uses an LED for presentation.

19. The object information acquiring apparatus according to claim 10, wherein
   the light quantity meter is arranged in the holder; and
   the light quantity meter is arranged at a side opposite to the irradiating end when the holder holds the photoacoustic probe.

20. The object information acquiring apparatus according to claim 1, wherein when the difference is less than the predetermined value, the processor acquires the information of the object by using the quantity of light which has been corrected based on values measured by the light quantity meter.

* * * * *